(12) United States Patent
Born (10) Patent No.: US 8,873,057 B2
(45) Date of Patent: Oct. 28, 2014

(54) VARIABLE PATH LENGTH PROBE

(75) Inventor: Christian Born, Holte (DK)

(73) Assignee: Foss Analytical A/S, Hilleroed (DK)

( * ) Notice: Subject to any disclaimer, the term of this patent is extended or adjusted under 35 U.S.C. 154(b) by 241 days.

(21) Appl. No.: 13/505,660

(22) PCT Filed: Dec. 10, 2009

(86) PCT No.: PCT/EP2009/066850

§ 371 (c)(1),
(2), (4) Date: May 2, 2012

(87) PCT Pub. No.: WO2011/069549

PCT Pub. Date: Jun. 16, 2011

(65) Prior Publication Data

US 2012/0218551 A1    Aug. 30, 2012

(51) Int. Cl.
*G01N 21/00* (2006.01)
*G01N 29/24* (2006.01)
*G01J 3/51* (2006.01)
*G01N 21/17* (2006.01)
*G01N 21/85* (2006.01)

(52) U.S. Cl.
CPC ........ *G01N 21/8507* (2013.01); *G01N 29/2418* (2013.01); *G01J 3/51* (2013.01); *G01N 21/1702* (2013.01)
USPC .......... 356/432; 356/413; 356/246; 356/326; 356/440; 356/436; 385/33; 250/339.07

(58) Field of Classification Search
CPC ............ G01N 21/1702; G01N 21/171; G01N 21/1717; G01N 21/255; G01N 29/2418; G01N 21/29; G01N 21/251; G01N 21/03; G01N 21/0303; G01J 3/51

USPC ................................. 356/432, 445–448, 413
See application file for complete search history.

(56) References Cited

U.S. PATENT DOCUMENTS

| 5,168,367 A | 12/1992 | O'Rourke et al. |
| 5,268,736 A * | 12/1993 | Prather ......................... 356/246 |
| 5,303,036 A | 4/1994 | McLachlan et al. |

(Continued)

FOREIGN PATENT DOCUMENTS

| DE | 19633963 A1 | 2/1998 |
| JP | 03-220444 | 9/1991 |

(Continued)

OTHER PUBLICATIONS

International Search Report.

*Primary Examiner* — Tarifur Chowdhury
*Assistant Examiner* — Isiaka Akanbi
(74) *Attorney, Agent, or Firm* — Harness, Dickey & Pierce, P.L.C.

(57) ABSTRACT

A probe having a probe head in which is formed an opening for receiving a sample to be analyzed, the head comprising a pair of optical interfaces disposed at an opposing inner surface of the opening to delimit a path for optical radiation through the opening, wherein one of the pair of optical interfaces comprises a transparent element adapted to permit optical radiation in one or more wavelength regions of interest to travel between the probe head and the opening, the optical probe comprising a movable diaphragm in which one of the pair of optical interfaces is located for movement therewith and an actuator operably connected to the diaphragm to control its movement so as to vary the path length wherein the probe head comprises a hinge system cooperable with the actuator to move the optical interface in the movable diaphragm in an arc to vary the path length.

16 Claims, 7 Drawing Sheets

(56) References Cited

U.S. PATENT DOCUMENTS

| | | | |
|---|---|---|---|
| 5,708,273 A | | 1/1998 | VonBargen |
| 6,128,079 A | | 10/2000 | McCloskey et al. |
| 6,137,108 A | * | 10/2000 | DeThomas et al. ...... 250/339.07 |
| 6,515,748 B2 | * | 2/2003 | Walker et al. ................. 356/436 |
| 8,556,813 B2 | * | 10/2013 | Cioanta et al. ................ 600/439 |
| 2012/0130649 A1 | * | 5/2012 | Salerno et al. ................. 702/23 |

FOREIGN PATENT DOCUMENTS

| | | |
|---|---|---|
| JP | 06-511081 | 12/1994 |
| JP | 08-035930 | 2/1996 |
| JP | 09-171142 | 6/1997 |
| JP | 2000-292346 | 10/2000 |
| WO | WO-9306458 A1 | 4/1993 |
| WO | WO-9612174 A1 | 4/1996 |

* cited by examiner

VARIABLE PATH LENGTH PROBE

The present invention relates to a probe having a variable transmission path length for use in optical analysis, particularly to a variable path length probe for the in-situ optical analysis of a material, especially a material in a process-line; reaction vessel; storage tank or other bulk container.

In industrial processes measurement and monitoring of the contents of a process line or a reaction vessel is often required. It may be important to be able to follow a reaction inside a process tank or monitor the contents of a process line as it passes through the processing system without conducting their contents through a complicated by-pass system of pipelines with a pump, valves and a flushing arrangement. Such monitoring providing the possibility for real-time process control. Furthermore, in the pharmaceutical or food preparation industry it may be important minimise the interaction of the contents with external equipment which may increase the risk of contamination so that in-situ analysis is preferable.

Optical spectrometric analysis, in particular infra-red analysis, is non-destructive and is particular suited for such measurement and monitoring since many materials, particularly organic materials, show highly characteristic infra-red absorption properties. Thus by measuring wavelength dependent infra-red absorption in a sample, either in transmission, reflection or transflectance analysis configurations, information concerning the physical structure and composition of the sample may be determined. Infra-red spectroscopy has been successfully utilised in the analysis of a wide variety of products including milk, cereal grains, oils, pharmaceuticals and bio-fuels.

It is known from WO 96/12174 to provide a probe having a probe head for location in a reaction vessel in order to determine the contents thereof by on-line optical analysis. The probe comprises a first light transmitting means in a tube which extends into the vessel and is intended for transmittance of light to an optical interface on an inner surface of a slot which is formed in the probe head in order to receive a sample for analysis. A reflector is located on an opposing inner surface of the slot to reflect light back towards the opposing window from where it is passed to outside the reaction vessel for analysis of the illuminated sample. An actuator is provided for altering the transmission path length between the light transmitting means in the tube and the reflector.

It is further known from U.S. Pat. No. 5,708,273 to provide a variable path length optical probe for analysis of a material in a process line. The probe comprises a probe head in which is formed a slotted opening for receiving a sample to be illuminated. Optical fibres terminate at a window in a first tubular housing which forms one side of the slotted opening and a mirror is arranged on a second tubular housing, disposed for sliding engagement with the first and forms the opposite side of the opening. The mirror and window together cooperate to delimit a light path through the opening and hence through the sample to be analysed. A manually operated actuator is connected to one or both housings for sliding one with respect to the other. The separation of the mirror and window is thereby regulated in order to vary the transmission path length of light through the slot.

According to a first aspect of the present invention there is provided a probe head in which is formed an opening for receiving a sample to be analysed, the head comprising a pair of optical interfaces each disposed at an opposing inner surface of the opening to delimit a transmission path through the opening, wherein at least one of the pair of optical interfaces comprises an element transparent to optical radiation in the wavelength disposed to permit optical radiation of interest to travel between internal the probe head and the opening. The optical probe further comprises a movable diaphragm, optionally in the form of a bellows, in which a one of the pair of optical interfaces is located for movement therewith and an actuator operably connected to the diaphragm to control its movement so as to vary the path length.

Optionally, the probe head further comprises a hinge system cooperable with the actuator to move the optical interface located in the diaphragm in an arc to vary the path length. The arcuate movement causes a lack of parallelism between the optical interfaces as the length of the light path varies and thereby reduces any adverse effects of reflections between the interfaces. Moreover, the hinge system may provide the diaphragm with increased stability to resist unwanted movement caused by external influences such as pressure changes or the force exerted by a flowing material in a pipe-line.

The diaphragm may comprise a flat, flexible sheet or alternatively a corrugated sheet or bellows to provide an increased range of movement and be formed so as to exert a bias force resisting extension of the diaphragm this can substitute for a separate biasing means, such as a spring, when such is required.

Optionally, the other of the pair of optical interfaces may also be located in an associated diaphragm which is also made movable so as to vary the path length of the transmission path through material between the interfaces.

These and further advantages will become clearer through a consideration of the following description of exemplary embodiments of the probe head according to the present invention which is made with reference to the drawings of the accompanying figures, of which:

FIG. 3 illustrate the probe head of FIGS. 1 and 2 in optical coupling to alternative analyser; in FIG. 3a to a local grating spectrometer and in FIG. 3b to a remote analyser.

Figure 1:
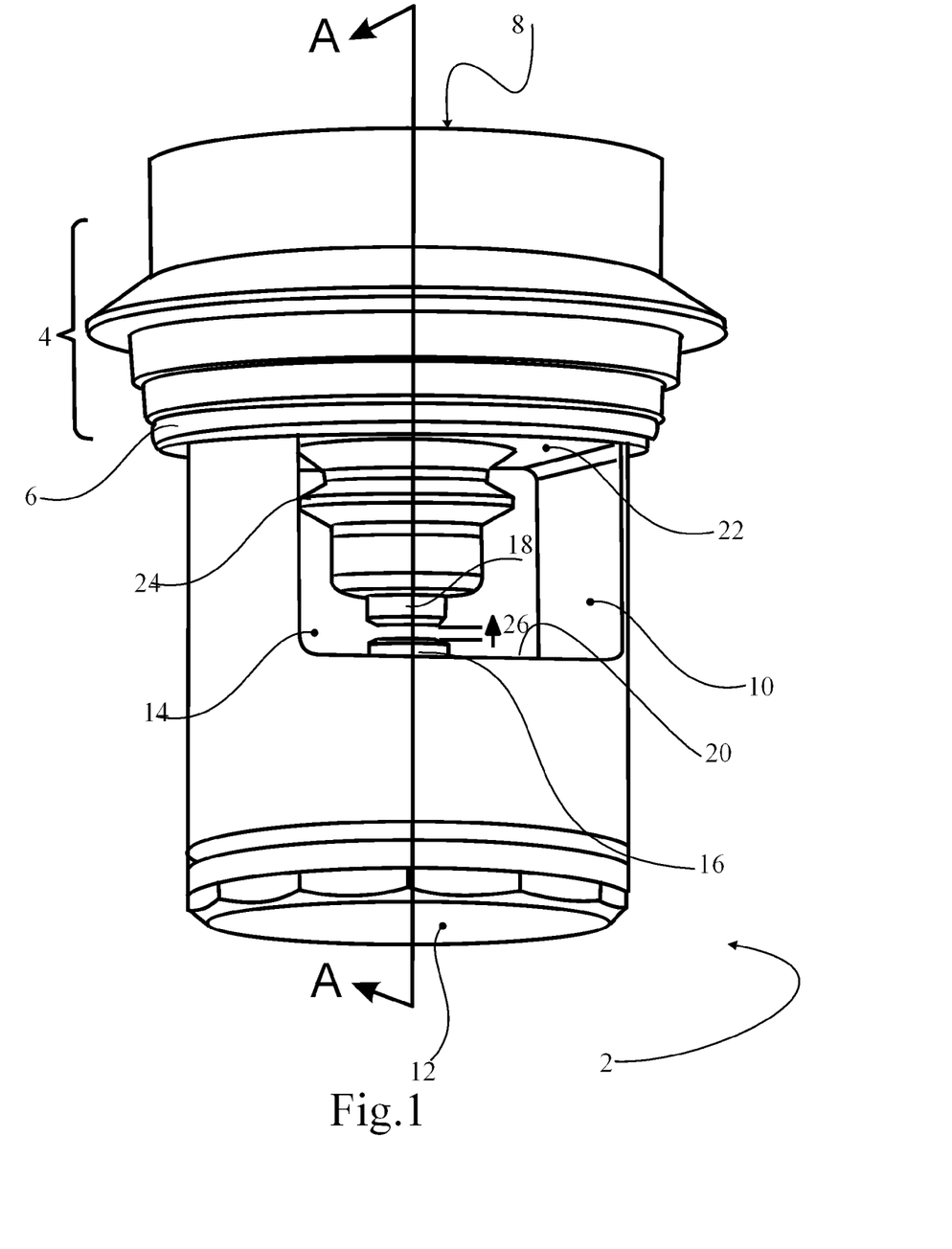
FIG. 1 illustrates a probe head according to the present invention.

Considering now FIG. 1 in which is illustrated an exemplary probe head 2 according to the present invention which is here intended for insertion into a process pipe-line, reaction vessel, storage tank or other bulk container. The probe head 2 is provided with an interface region 4 including here a sealing ring 6 and which is intended to interface with and seal against a corresponding interface on, for example, the process pipe-line (not shown). This interface region 4 serves as a boundary separating a proximal end 8 of the probe head 2 from a distal end 12. The proximal end 8 is, in use, located outside the pipe-line whilst the distal end 12 is intended for immersion in the material, typically flowing material, in the pipe-line. An opening, in the present embodiment a slot 10, is located in the probe head 2 after the interface region 6 and towards the distal end 12 of the probe head 2. The slot 10 provides a sample space 14 into which a portion of material in the process-line can pass, in the present embodiment flow through, for analysis. A pair of optical interfaces 16,18 are located in opposition to one another within the slot 10 at respective opposing inner surfaces 20, 22 of the slot 10. In the present embodiment a single one of the optical interfaces 18 is shown to be located in a movable diaphragm, here corrugated to form a bellows diaphragm 24, but it will be appreciated that the other of the pair of optical interfaces 16 may also be located in its own movable diaphragm. The optical interfaces 16, 18 cooperate to together delimit a path length (illustrated generally by arrow 26) for radiation through the opening and hence through a sample of material for analysis located in the slot 10 between the optical interfaces 16,18.

The actual length of the transmission path will depend on the material being analysed and particularly on the wavelength region of optical energy being employed in the analysis. By way of example only, the probe head 2 of the present embodiment may be configured for analysis using optical energy within the mid infra-red wavelength region. In this configuration the gap between the optical interfaces 16,18 is of the order of 40 μm and is adjustable as described below to around 20 μm. In such a circumstance, where the expected variation in optical path length is suitable, the corrugated diaphragm may conveniently be replaced with a diaphragm constructed as an essentially flat sheet of material.

The small relative displacement of the optical interfaces 16,18 and the general requirement of few sealings, whether dynamic or static, make it advantageous to mount a one of the interfaces 18 in the flexible, typically metallic, bellows diaphragm 24. This bellows diaphragm 24 can either be a standard bellows which is welded to a rim of the appropriate inner surface 10 and the optical interface 18 or all can be integrated in to one part as is illustrated in the present embodiment. In either case the bellows diaphragm 24 may be made so stiff that it by pre tension during assembly it can also act as return spring for an actuator. The construction can advantageously be made sufficiently stable so that the internal flow of material in the pipe-line, pressure fluctuations, etc will not have any significant influence on the relative positions of the interfaces 16,18.

Figure 2:
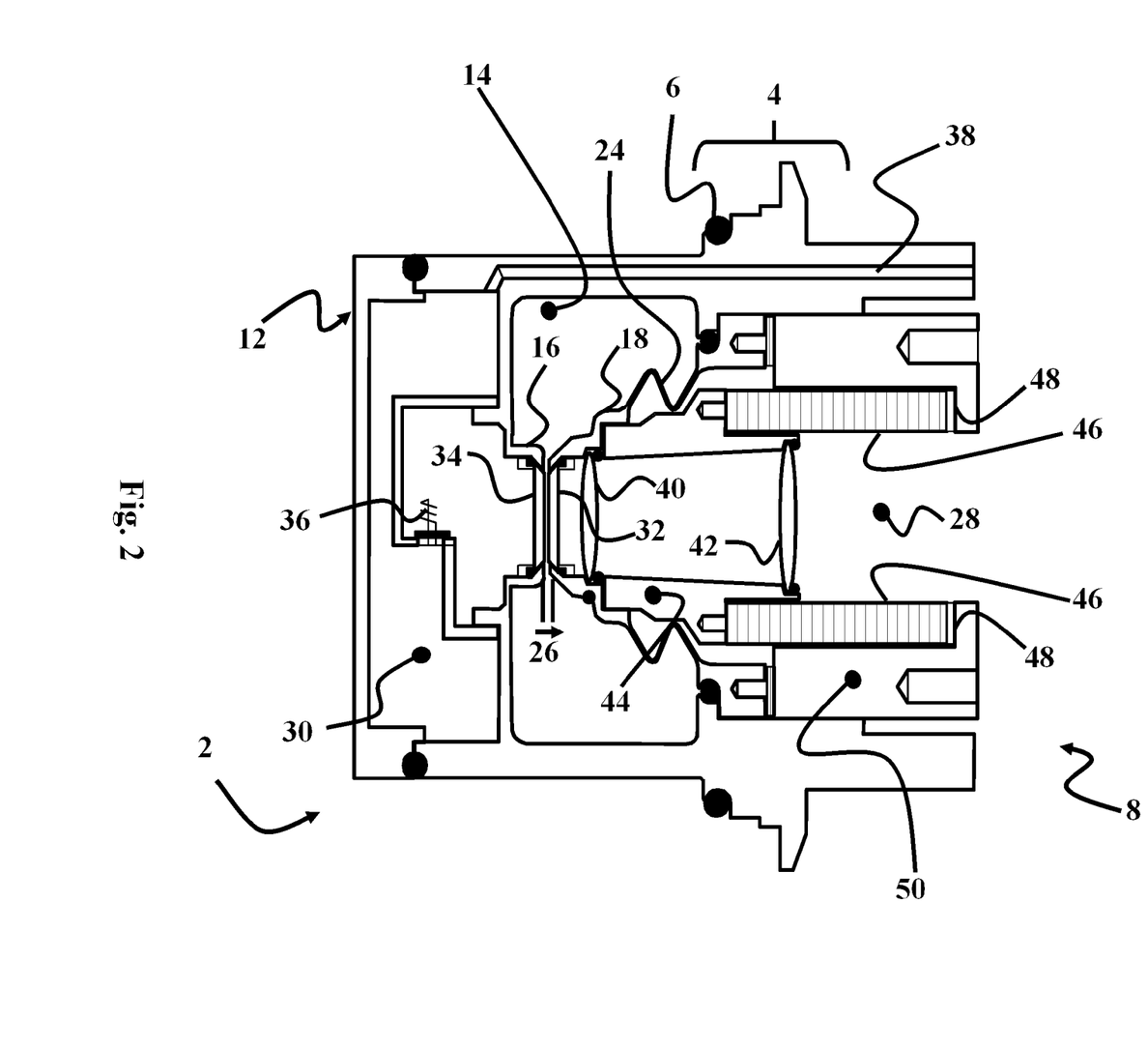
FIG. 2 illustrates a section A-A through the probe head of FIG. 1.

Turning now FIG. 2 which is a section A-A through the probe head 2 of FIG. 1 and in which elements common to the figures are given the same reference numerals. The probe head 2 comprises a first cavity 28 and a second cavity 30 separated by the sample space 14. The optical interface 18 comprises a first window 32 which, in cooperation with the bellows diaphragm 24, seals the first cavity 28 against ingress of material from the sample space 14. The optical interface 16 is, in the present embodiment, shown to comprise a second window 34 which seals the second cavity 30 against ingress of material from the sample space 14.

A source of optical radiation 34, here a source of mid infra-red radiation is located in the second cavity 30 to generate optical radiation for transmission through the second window 34, along the light path 26 delimited by the second and the first windows 34,32 and in to the first cavity 28 through the first window 32. The source of optical radiation 36 is provided with power from an external source (not shown) via electrical connectors which pass through a conduit 38 in the probe head 2.

In an alternative embodiment the source 36 may be replaced by a suitable fibre optic which may be passed through the conduit 38 and terminated in the second cavity 30 behind the second window 34.

Focusing optics 40,42 are provided in a slidable mount 44 and focuses light from the source 36 after it having traversed the light path 26. The mount 44 is arranged to provide a mechanical coupling between the bellows diaphragm (here to the optical interface 18) and an actuator, here a piezo-actuator 46. Shims 48 may be provided to provide grove adjustment of the angle of the first window 32 with respect to the second window 34 and are here shown disposed between one end of the actuator 46 and a fixed internal portion 50 of the probe head 2.

In this embodiment a circular piezo-actuator 46 is chosen as this is very precise, fast and has a high repeatability. The stroke and lifting/relaxing speed can be controlled electrically. This actuator 46 is also capable of maintaining a lift that is parallel to within microns. This piezo-actuator is a standard product and a proposal could be one with an outer diameter of around 20 mm and inner diameter of 12 mm. This type and size is very powerful with a blocking force of around 8000 N which opens for the use of a very stiff return spring. In this design it is also easy to make an initial adjustment by the shims 48 which is much more stable, firm and reliable than adjusting screws or the like, which of course may substitute for the shims 48.

Figure 3A:
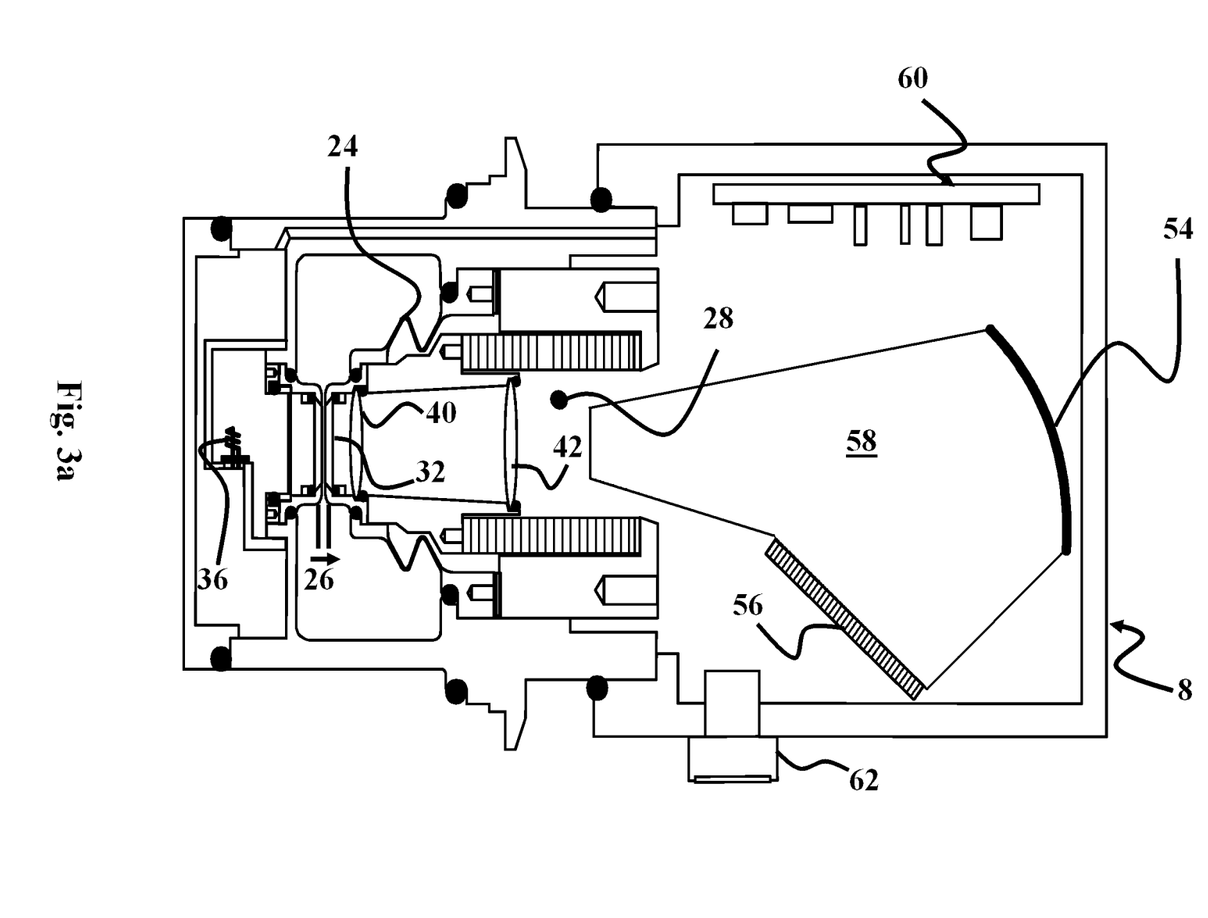

FIG. 3 illustrates different exemplary constructions of the proximal end 8 of the probe head 2 of FIGS. 1 and 2. In FIG. 3a the probe head 2 of FIGS. 1 and 2 is shown with its proximal end 8 formed as an enclosure for a local grating spectrometer, which spectrometer is indicated generally by numeral 52.

Contained in the proximal end 8 and forming a part of the spectrometer 52 is a static diffraction grating 54 and complementary detector array 56. The grating 54 and array being mutually arranged in a conventional configuration such that light received onto the grating 54 is dispersed according to its wavelength and each wavelength region made incident at a different associated region of the detector array 56. In this manner wavelength dependent intensity measurements may be performed on the received light and compositional information about the material within the sample space 14 included in the light path 26 may be determined.

As is known in the art, an optical conditioner, here a wedge waveguide 58, is also provided in the present embodiment as an element of the spectrometer 52 and connects the grating 54 and the detector array 56 optically. Usefully this optical conditioner 58 may be configured to present incident light in an optimal manner first to the grating 54 and then to the detector array 56 The focussing optics 40,42 serve to focus light entering the first cavity 28 through the window 32 into the waveguide 58. The light is then guided on to the grating 54 and the dispersed light from the grating 54 to the detector array 56.

The grating spectrometer 52 configuration of the probe head 2 is very attractive as the only moving part is the diaphragm 24 and window 32 arrangement. It is therefore expected to be very insensitive to vibrations and is also easy to handle during calibration or control where an operator may need to dismount the sensor from the pipe-line.

Control electronics for one or both the detector array 56 and the light source 36 may be conveniently housed by the enclosure 8. A drying cartridge 62, such as one filled with the known desiccant, Silica gel, may optionally be provided to maintain inside the enclosure 8 dry.

Figure 3B:
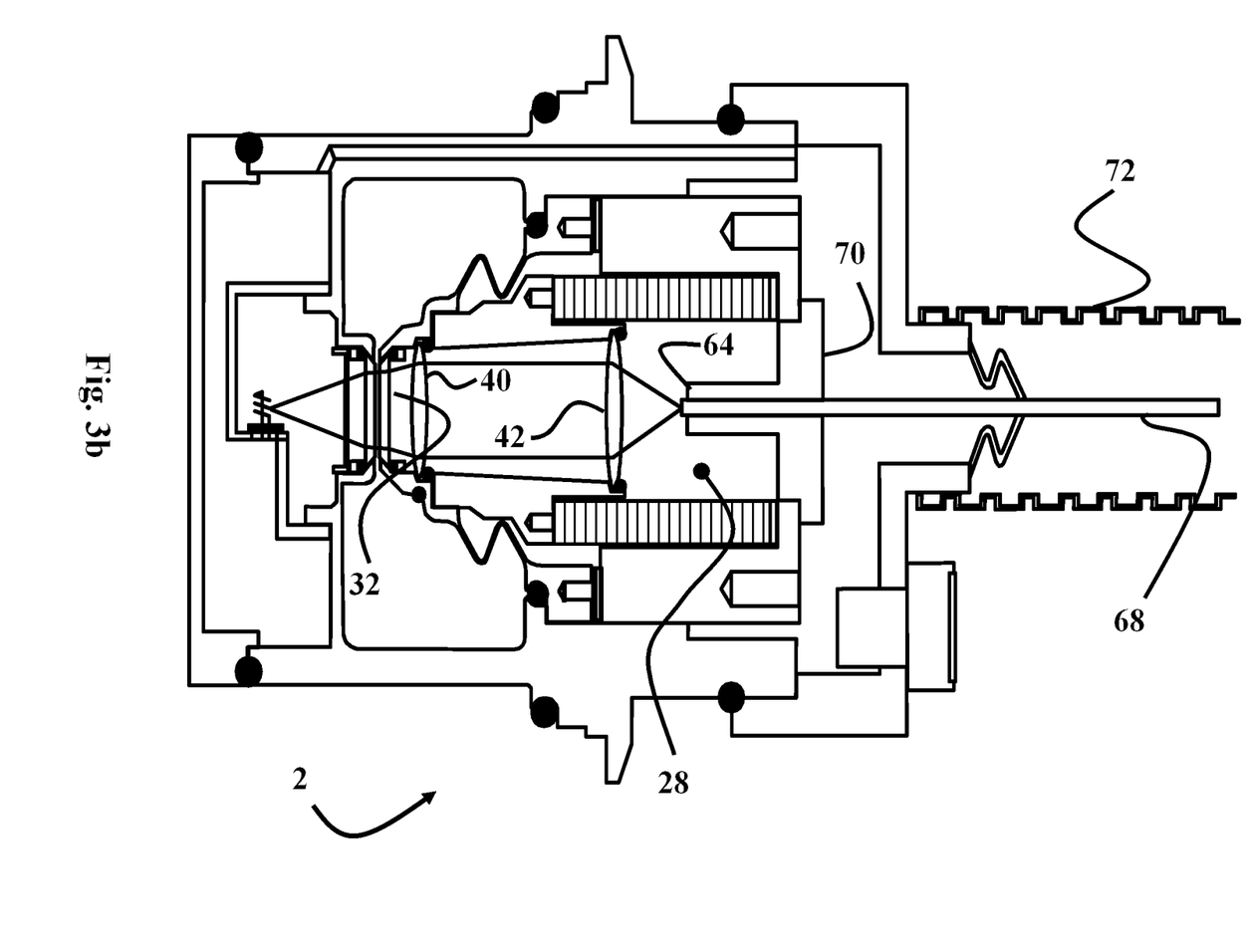

In FIG. 3b the probe head 2 of FIGS. 1 and 2 is shown with its proximal end 8 formed as an enclosure for an end 64 of a fibre optic 68, which end 64 is held within the probe head 2 fixed and centrally by a support 70.

In the present embodiment the focussing optics 40,42 act to focus light which enters the first cavity 28 through window 32 onto the end 64 of the fibre optic 68. The fibre optic 68 acts as an optical coupling between the probe head 2 and a remote analyser (not shown) such as a Fourier Transform analyser, spectrometer or other analyser suitable for use in the determination of compositional or other (presence or absence of material say) information from the so collected light. This arrangement has the advantages of few moving parts and is relatively compact in design compared with say, the spectrometer system of FIG. 3a.

In the presently described embodiment, as used with mid infra-red light, the fibre optic 68 is relatively brittle and susceptible to mechanical damage from, for example, vibrations in the operating environment of the probe head 2. Here a flexible tubing 72 may be advantageously employed in order to afford some mechanical protection to the fibre optic 68. Indeed such protection may be employed usefully with other types of fibre optic.

Figure 4:
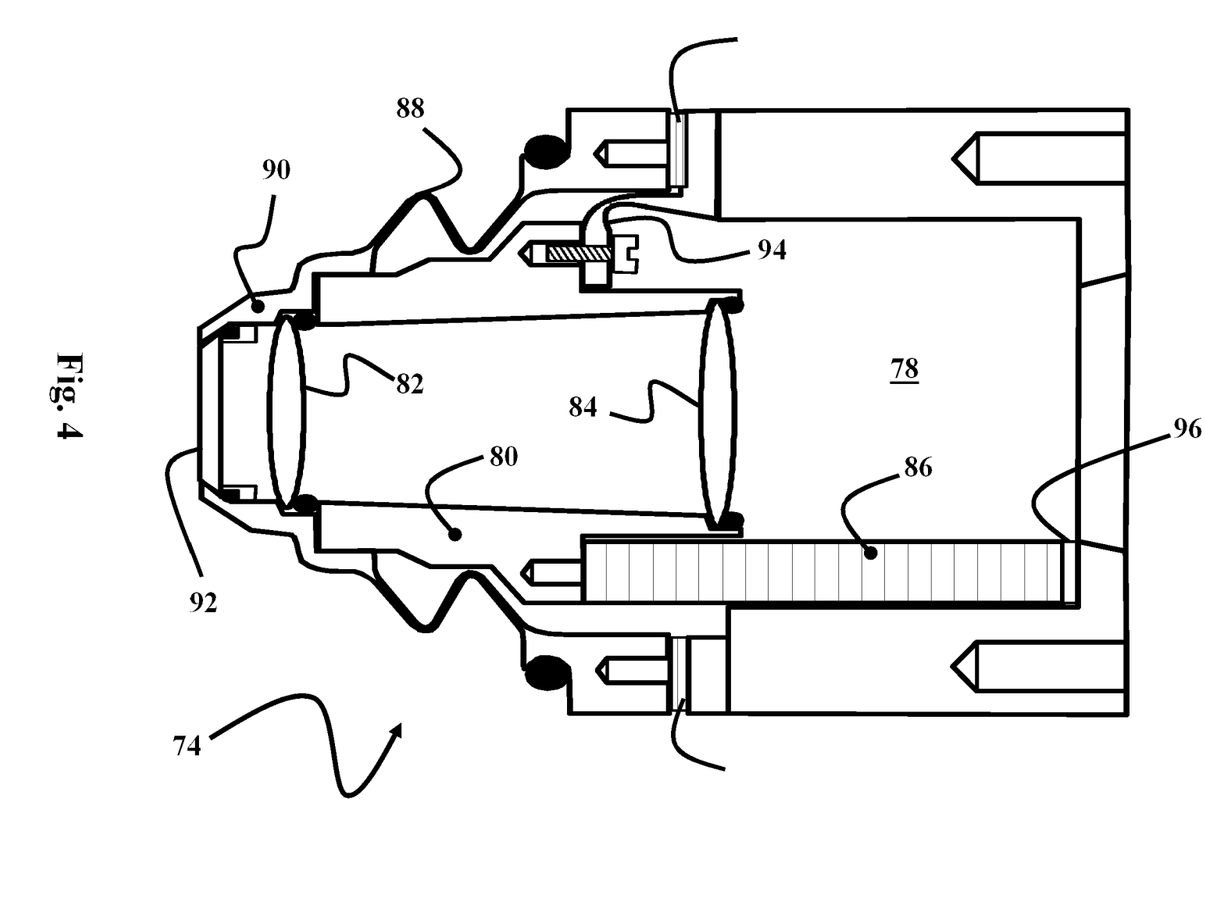
FIG. 4 illustrates a further exemplary probe head according to the present invention.

A second exemplary embodiment of a probe head 74 according to the present invention is illustrated in FIG. 4 and may, as the skilled person will be aware, readily substitute for the probe head 2 in the assemblies described in FIG. 3.

Illustrated in FIG. 4 is that portion of the probe head 74 which constitutes a first cavity 78 of the probe head 74 similar to the first cavity 28 of the probe head 2 of FIG. 2. In the present embodiment, similar to FIG. 2 but not shown, the probe head 74 also comprises a second cavity in which a source of optical radiation is located.

Also similar to the probe head 2 of FIG. 2 the first cavity 78 of present probe head 74 embodiment contains a slidable mount 80 for holding focussing optics 82,84 and providing a mechanical contact between an actuator 86, here a single stacked piezo-electric actuator as opposed to the circular one used in the embodiment of FIG. 2, and a bellows diaphragm 88. Similar to the embodiment of FIG. 2 an optical interface 90 comprising a window 92 is held in the bellows diaphragm 88 for movement therewith as the actuator 86 operates to push the slidable mount 80 to extend the bellows diaphragm 88, acting against the return spring formed into the bellows diaphragm. A separate return spring may additionally or alternatively be provided to tend to bias the bellows diaphragm 88 towards a contracted position.

A hinge system 94 is provided in mechanical connection to one side of the bellows diaphragm 88, here in the present embodiment in mechanical connection to one side of the slidable mount 80, generally opposing the point at which the actuator 86 is set to apply a force to push the bellows diaphragm 88.

The hinge system 94 advantageously provides an increase stiffness to the bellows diaphragm 88 which tends to resist any movement of the window 92 that may be caused by the internal flow of material in the pipe-line, pressure fluctuations etc. The hinge system 94 cooperates with the actuator 86 to provide a small angular movement of the window 92 relative to the other window of the second cavity as the actuator moves the bellows diaphragm 88. This creates a limited non-parallelism between the two windows which may advantageously prevent unwanted reflection artefacts being created between the windows.

The hinge system 94 of the present embodiment is shown to comprise a single hinge but a plurality of hinges, for example two narrow hinges radially separated by an angle of between 30 to 60 degrees, may be employed to provide an increased stiffness.

Shims 96 may be provided to make a grove angular adjustment to the window 92 and additional shims 98 may be employed to set a base separation between the widows.

Whilst the embodiments discussed above describe probe heads for transmission measurements in which windows are employed in an optical interface to define a light path through a sample it will be appreciated that other optical interfaces may be provided by which transmission measurements may be effected in a variable path length optical probe according to the present invention. One or both of the windows may be replaced with a lens or other transparent optical element; a one of the optical elements may be replaced with a reflector, the second cavity removed and both light generation and collection made in the first cavity, perhaps using a suitably configured fibre optic arrangement. In a further modification of the probe according to the present invention the other optical interface of the pair may also be incorporated into its own movable diaphragm, either similar to the ones described in relation to the exemplary embodiments set out herein or perhaps alternatively formed as a flat sheet of flexible material such as a metal sheet.

Figure 5:
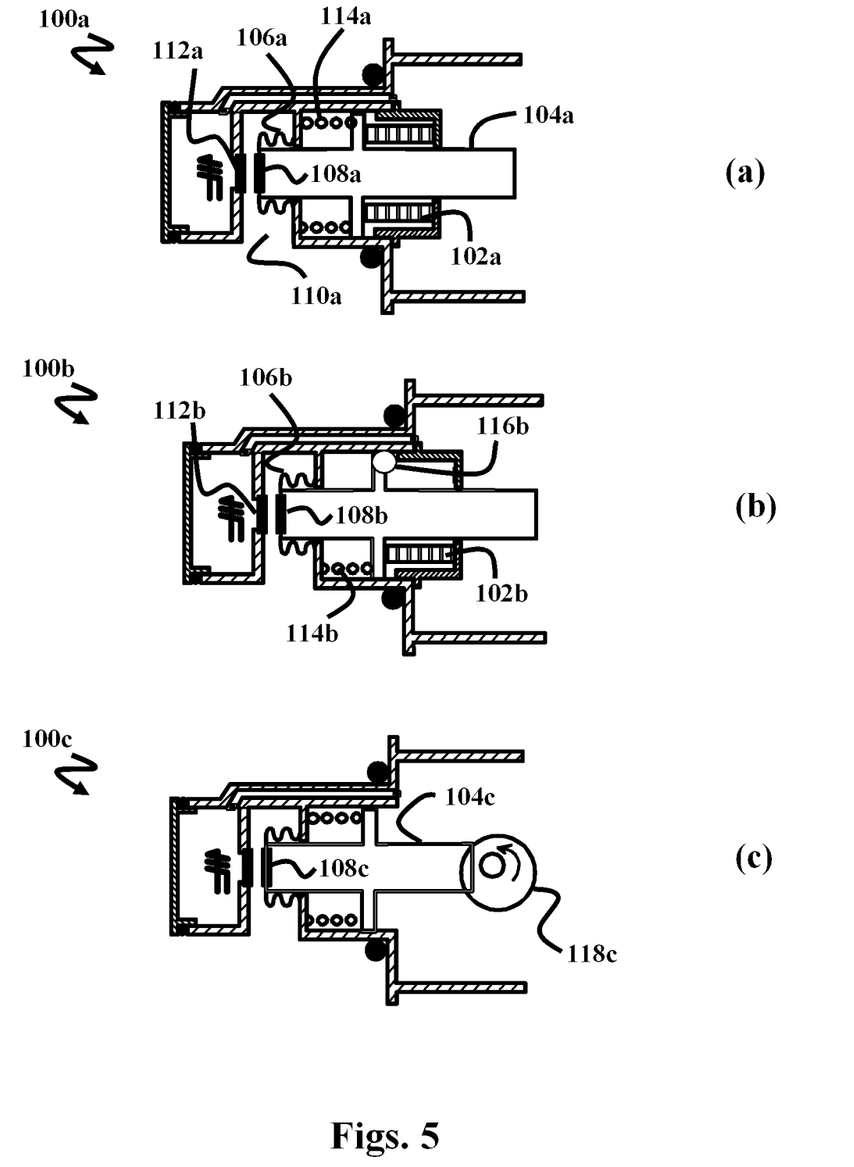
FIG. 5 illustrate a number of alternative actuators for moving the diaphragm.

Other actuators may also be used as a substitute for the piezo-actuators described with reference to FIGS. 2 and 4 above with departing from the invention as claimed. Examples of four further actuators that are suitable for use in the present invention are described in outline with reference to the illustrations of FIG. 5. For ease of comparison with the previously described embodiments FIG. 5a illustrates a probe head 100a which operates generally according to the description of the probe head 2 given above and FIG. 5b illustrates a probe head 100b which operates generally according to the description of the probe head 74 given above.

The probe head 100a of FIG. 5a employs a circular piezo-actuator 102a to act on a hollow pipe 104a which is attached towards one end to an adjustable bellows diaphragm 106a in which is located a window 108a. The window 108a is disposed within a slot 110a formed in the probe head 100a for receiving a sample material and is opposing a second window 112a. The windows 108a and 112a delimiting a light path between a portion of the sample material to be analysed. Different to the probe head 2 earlier described, a spring 114a is also provided to substitute, or at least augment, the return bias spring force of the bellows diaphragm 106a tending to contract the bellows diaphragm 106a.

The probe head 100b of FIG. 5b differs from that of FIG. 5a in that a single stacked piezo-actuator 102b replaces the circular one 102a of FIG. 5a and in that a hinge 116b is provided cooperable with the actuator 102b to cause a window 108b located in a bellows diaphragm 106b to undergo a small angular movement as the bellows diaphragm is expanded to reduce the light path between opposing windows 108b, 112b. A spring 114b is again provided to tend to bias the bellows diaphragm 106b towards a contracted state.

Considering now the probe head 100c illustrated in FIG. 5c, the actuator comprises a cam 118c directly coupled to the hollow light-pipe 104c so that as the cam 118c rotates the light-pipe 104c and hence the window 108c undergoes reciprocal movement to vary the light-path. In the probe head 100d, illustrated in FIG. 5d a cam 118d acts indirectly on the light-pipe 104d via a flexible mechanical coupling 120d. The coupling 120d is fixed towards one end at the light-pipe 104d and also towards the opposite end. As the cam 118d rotates the mechanical coupling 120d is caused to flex, moving the light-pipe 104d to vary the light-path.

According to the embodiment of a probe head 100e which is illustrated in FIG. 5e a magnet or solenoid actuator (here a magnet) 122e is provided to act directly on the light-pipe 104e causing it to move to vary the path length of the transmission path as the actuator is energised and de-energised. In the probe head 100f of FIG. 5f a magnet or solenoid actuator (here a solenoid) 122f acts indirectly on the light-pipe 104f via a flexible mechanical coupling 120f. The coupling 120f is fixed towards one end at the light-pipe 104f and also towards the opposite end. As the actuator is energised and de-energised the mechanical coupling 120f is caused to flex, moving the light-pipe 104f to vary the length of the path.

By way of example, the probe head according to the present invention may be usefully employed to make optical measurements at two or more different path lengths and the results used to make an analysis in which compensation for drift is made without recourse to the use of a reference sample for so-called "zero setting". The methodology and rational applied here is similar to that described in WO 2006/058741, the contents of which are incorporated herein by reference, in relation to multiple path length, typically dual path length, measurements made using a hinged cuvette sample holder to achieve the variable path length through the sample to be analysed. Thus the probe head according to the present invention may be made to present a plurality of different path lengths to radiation emitted from the source. A value is calculated which is dependent on the ratio of intensities of radiation having traversed two path lengths of the plurality of different path lengths for a same one of the one or more emitted wavelengths and from which may be generated one or both quantitative and qualitative indications of the sample.

The invention claimed is:

1. A probe, comprising:
a probe head including,
an opening for receiving a sample to be analysed,
a pair of optical interfaces each disposed at an opposing inner surface of the opening to delimit a path for optical radiation through the opening, wherein at least one of the pair of optical interfaces comprises an optically transparent element adapted to permit optical radiation in one or more wavelength regions of interest to travel between an internal section of the probe head and the opening,
a movable diaphragm in which one of the pair of optical interfaces is located for movement therewith,
an actuator operably connected to the diaphragm and configured to control a movement of the diaphragm so as to vary a length of the path, and
a hinge system configured to, in cooperation with the actuator, move the optical interface located in the movable diaphragm in an arc to vary the path length and to create a non-parallelism between the optical interfaces.

2. A probe as claimed in claim 1, wherein the movable diaphragm is a bellows.

3. A probe as claimed in claim 1, wherein the optically transparent element is located in the movable diaphragm.

4. A probe as claimed in claim 1, wherein the other of the pair of optical interfaces is located in a second diaphragm that is movable to vary the path length.

5. A probe as claimed in claim 1, wherein the other of the pair of optical interfaces also comprises an optically transparent element adapted to permit light to travel between the internal section of the probe head and the opening.

6. A probe as claimed in claim 5, further comprising:
a source of optical energy configured to emit the optical radiation, the source of optical energy being disposed in the probe head behind one of the optically transparent elements; and
a complementary optical energy collector disposed behind the other of the optically transparent elements and configured to collect optical energy from the source after having traversed the path for optical radiation.

7. A probe as claimed in claim 1, wherein the other optical interface comprises a reflector disposed to reflect light towards the optically transparent element.

8. A probe as claimed in claim 1, wherein the actuator comprises a piezoelectric actuator.

9. A probe as claimed in claim 1, wherein the probe head further comprises a grating spectrometer housed in a proximal end of the probe head, the grating spectrometer being configured to receive light having passed through the optical interface located in the diaphragm after traversing the path for optical radiation.

10. A probe as claimed in claim 1, wherein the actuator is located within the probe head.

11. A probe head, comprising:
an opening for receiving a sample to be analysed;
a pair of optical interfaces each disposed at an opposing inner surface of the opening to delimit a path for optical radiation through the opening, wherein at least one of the optical interfaces comprises an optically transparent element adapted to permit optical radiation in one or more wavelength regions of interest;
a movable diaphragm in which one of the pair of optical interfaces is located for movement therewith;
a piezoelectric actuator connected to the movable diaphragm and configured to control a movement of the diaphragm so as to vary a length of the path; and
a hinge system configured to, in cooperation with the piezoelectric actuator, move the optical interface located in the movable diaphragm in an arc to vary the path length and to create a non-parallelism between the optical interfaces.

12. A probe head as claimed in claim 11, further comprising:
a slideable mount connected to the diaphragm and the piezoelectric actuator such that the piezoelectric actuator is configured to control the movement of the diaphragm by exerting a force on the mount.

13. A probe head as claimed in claim 12, wherein the piezoelectric actuator is a single stacked piezoelectric actuator, and the single stacked piezoelectric actuator and the hinge system are located on opposite sides of the mount.

14. A probe head as claimed in claim 12, wherein the piezoelectric actuator is a circular piezoelectric actuator configured to exert the force on opposite sides of the mount.

15. A probe head as claimed in claim 12, further comprising:
a source configured to emit the optical radiation, the source being disposed behind one of the optically transparent elements; and
a collector configured to collect the emitted optical radiation, the collector being disposed behind the other of the optically transparent elements.

16. A probe head as claimed in claim 15, wherein the mount includes at least one focussing optical element configured to focus the optical radiation toward the collector.

* * * * *